United States Patent
Benetti et al.

(10) Patent No.: US 7,932,337 B2
(45) Date of Patent: Apr. 26, 2011

(54) INVERSE EMULSIONS AS THICKENERS FOR COSMETICS

(75) Inventors: Arianna Benetti, Gallarate (IT); Gianmarco Polotti, Sesto San Giovanni (IT); Giuseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 837 days.

(21) Appl. No.: 11/767,177

(22) Filed: Jun. 22, 2007

(65) Prior Publication Data
US 2007/0258927 A1    Nov. 8, 2007

Related U.S. Application Data

(63) Continuation-in-part of application No. PCT/EP2005/057001, filed on Dec. 21, 2005.

(51) Int. Cl.
*C08F 128/02* (2006.01)
(52) U.S. Cl. .......... 526/288; 526/292.95; 526/306; 526/310; 526/312
(58) Field of Classification Search .......... 526/288, 526/292.95, 306, 310, 312
See application file for complete search history.

(56) References Cited

U.S. PATENT DOCUMENTS

| | | |
|---|---|---|
| 6,187,887 B1 * | 2/2001 | Albrecht et al. ............ 526/264 |
| 6,197,287 B1 | 3/2001 | Mallo et al. |
| 6,329,483 B1 | 12/2001 | Schade et al. |
| 6,375,959 B1 | 4/2002 | Mallo et al. |
| 6,395,853 B1 * | 5/2002 | Oswald et al. ............ 526/307.2 |
| 7,238,760 B2 * | 7/2007 | Schinabeck et al. ........ 526/288 |
| 2001/0023284 A1 | 9/2001 | Candau et al. |
| 2003/0223951 A1 | 12/2003 | Geary et al. |
| 2005/0143558 A1 | 6/2005 | Rinaldi et al. |
| 2005/0171344 A1 | 8/2005 | Rinaldi et al. |
| 2006/0147404 A1 | 7/2006 | Benetti et al. |
| 2006/0275240 A1 | 12/2006 | Polotti et al. |

FOREIGN PATENT DOCUMENTS

| | | |
|---|---|---|
| EP | 0503853 | 9/1992 |
| FR | 2802936 | 6/2001 |
| WO | 2004063228 | 7/2004 |
| WO | 2004113393 | 12/2004 |

* cited by examiner

*Primary Examiner* — Bernard Lipman
(74) *Attorney, Agent, or Firm* — Mossman, Kumar & Tyler PC

(57) ABSTRACT

Inverse emulsions useful for the preparation of cosmetic formulations can be prepared wherein the weight ratio between the aqueous phase and the organic phase is from 4:1 and 2:1 and containing from 20 to 70% by weight of an acrylic polymer obtained by inverse emulsion polymerisation of i. from 55 to 75% by weight of an anionic acrylic monomer containing a strongly acidic functional group;

ii. from 0.1 to 5% by weight of a cationic acrylic monomer of the formula (I)

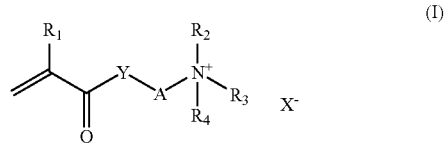

wherein
$R_1$ is hydrogen or methyl;
$R_2$, $R_3$, $R_4$ are, one independently of the others, hydrogen or $C_1$-$C_4$ alkyl;
Y is NH or O;
A is a $C_1$-$C_6$ alkylene;

iii. from 25 to 45% by weight of a $C_3$-$C_5$ anionic acrylic monomer containing a carboxylic group.

6 Claims, No Drawings

INVERSE EMULSIONS AS THICKENERS FOR COSMETICS

CROSS REFERENCE TO RELATED APPLICATION

This Application is a Continuation-In-Part of PCT Application No. PCT/EP2005/057001 which was filed on 21 Dec. 2005 designating the United States as a Designated State and claiming priority from Italian Patent Application Number IT-VA2004A000063 which was filed on 23 Dec. 2004.

BACKGROUND OF THE INVENTION

1. Field of the Invention

The present invention relates to inverse emulsions useful as thickener in cosmetic formulations and to the procedure for their preparation.

2. Background of the Art

The inverse emulsions of the invention comprise a polymer obtained by polymerization of an acrylic anionic monomers containing a strong acid functionality (and more specifically a sulfonic functional group), and one or more cationic monomer.

The inverse emulsions of the invention possess high skin and hair compatibility, which makes them particularly suited for the preparation of cosmetic formulations, and exhibit good thickening properties and stability over time.

With the expression "cosmetic formulations" we mean the products normally used for personal care, such as body and face creams, hair gels and lotions, hair coloring and bleaching creams, sunscreen compositions, make-up products, cleansing, moisturizing and perspiring fluids and other products for similar applications.

It is known that a technical problem often encountered in the cosmetic industry is to obtain high viscous formulations (pastes, gels) stable over time and exhibiting high compatibility with skin and hair.

An essential characteristic of the thickeners employed in cosmetic formulations is that they manifest their thickening capability without negatively altering the other properties of the formulations.

In the specialized literature many methods are reported to regulate the rheological properties of different formulations, often including the use of polymers in the form of inverse emulsion (an inverse emulsion is an emulsion containing both an oil-in-water emulsifier and a water-in-oil emulsifier, wherein the aqueous phase is dispersed in the organic phase in very small drops), but the synthetic thickeners for cosmetics of the present invention are never described.

We cite as an example:

EP 503853, wherein an inverse emulsion containing a polymer comprising units deriving from acrylamide, 2-acrylamido-2-methylpropanesulfonic acid and a polyfunctional monomer is described; a disadvantage of the inverse emulsions of EP 503853 is the fact that they contain traces of acrylamide, a toxic substance which is unacceptable by the present European legislative trend;

U.S. Pat. Nos. 6,375,959 and 6,197,287 wherein a procedure for the preparation of cross-linked or branched polyelectrolytes based on strongly acidic monomers and other monomers, but not acrylamide, in the form of an inverse emulsion, is described;

U.S. Pat. No. 6,329,483, wherein copolymers of carboxylic acids and quaternary ammonium compounds and the preparation of gels and emulsions containing the same is described;

US 2001/0023284, wherein copolymers of a neutral monomer (N-alkylacrylamide) with one or more monomers selected among cationic monomers, monomers bearing strongly acidic functional groups and monomers bearing weakly acidic functional groups are described.

The Applicant described in its international application PCT/IT03/00389 thickening inverse emulsions containing an acrylic polymer obtained from the inverse emulsion polymerization of an anionic acrylic monomer containing a weakly acidic functional group, an anionic acrylic monomer having a strongly acidic functional group and a cationic acrylic monomer.

It is still desirable in the cosmetic field to have thickeners in the form of stable emulsion that are able to give stable cosmetic formulations, and that, in addition to a good thickening efficiency in different conditions and ease of use, exhibit an improved compatibility with skin and hairs.

SUMMARY OF THE INVENTION

In one embodiment, the invention is an inverse emulsion comprising an aqueous phase and an organic phase, wherein the weight ratio of the aqueous phase to the organic phase is from 4:1 to 2:1 and the inverse emulsion includes from 20 to 70% by weight of an acrylic polymer obtained by inverse emulsion polymerization of:
(i) from 90 to 99.9% by weight of an anionic acrylic monomer containing a strongly acidic functional group;
(ii) from 0.1 to 10% by weight of a cationic acrylic monomer of the formula (I):

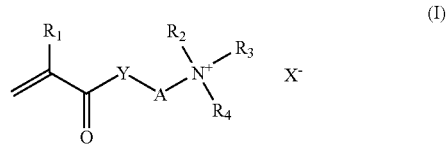

wherein:
$R_1$ is hydrogen or methyl;
$R_2$, $R_3$, and $R_4$ are, one independently of the others, hydrogen or $C_1$-$C_4$ alkyl;
Y is NH or O;
A is a $C_1$-$C_6$ alkylene; and
X is an anion.

In another embodiment, the invention is a procedure for the preparation of an inverse emulsion comprising:
a. preparing a composition comprising from 40 to 60% by weight of water, and from 60 to 40% by weight a mixture of acrylic monomers wherein the acrylic monomers used are:
(i) from 90 to 99.9% by weight of an anionic acrylic monomer containing a strongly acidic functional group; and
(ii) from 0.1 to 10% by weight of a cationic acrylic monomer of the formula (I):

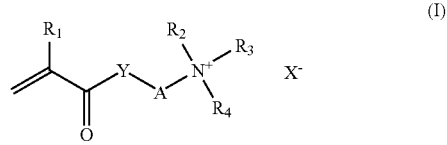

wherein:
R$_1$ is hydrogen or methyl;
R$_2$, R$_3$, and R$_4$ are, one independently of the others, hydrogen or C$_1$-C$_4$ alkyl;
Y is NH or O;
A is a C$_1$-C$_6$ alkylene; and
X is an anion;

b. adding to the composition prepared in a, an aqueous solution of an alkali to regulate the pH between 4 and 7, a cross-linking agent and an initiator of radical polymerization while maintaining the temperature between 3 and 7° C.;

c. preparing an organic phase containing one or more water-in-oil emulsifiers;

d. introducing the mixture obtained in b into the organic phase prepared in c and emulsifying the two phases by vigorous stirring;

e. initiating the polymerization and completing it while maintaining the temperature between 55 and 95° C. under vigorous stirring; and f. cooling the reaction mixture to 35-45° C. and adding an oil-in-water emulsifier.

In still another embodiment, the invention is a cosmetic prepared using an inverse emulsion comprising an aqueous phase and an organic phase, wherein the weight ratio of the aqueous phase to the organic phase is from 4:1 to 2:1 and the inverse emulsion includes from 20 to 70% by weight of an acrylic polymer obtained by inverse emulsion polymerization of:

(i) from 90 to 99.9% by weight of an anionic acrylic monomer containing a strongly acidic functional group;
(ii) from 0.1 to 10% by weight of a cationic acrylic monomer of the formula (I):

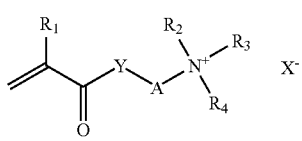

wherein:
R$_1$ is hydrogen or methyl;
R$_2$, R$_3$, and R$_4$ are, one independently of the others, hydrogen or C$_1$-C$_4$ alkyl;
Y is NH or O;
A is a C$_1$-C$_6$ alkylene; and
X is an anion.

DETAILED DESCRIPTION OF THE INVENTION

With the expression "stable emulsion" we mean an emulsion that in the normal storing conditions (from −10° C. to 40° C.) and for the usual lifetime (180-360 days) does not show phase separation, sediment, formation of floating pellicles and lumps.

With the expression "stable cosmetic product" we mean a cosmetic formulation that in the above said conditions and lifetime does not show phase separation, sediment, formation of floating pellicles and lumps.

By cosmetic product with high compatibility with skin and hair we mean a product that is easily absorbed through a keratinous substrate while making changes in the touch, in moisturization and perspiration, and improving the general sensorial characteristics without altering the physiological pH.

In developing its research the Applicant has now found that it is possible to obtain excellent results by using in polymerization exclusively anionic acrylic monomers containing a strongly acidic functional group and at least a cationic monomer of the formula (I)

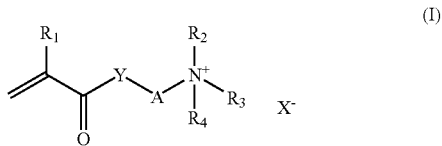

wherein
R$_1$ is hydrogen or methyl;
R$_2$, R$_3$, R$_4$ are, one independently of the others, hydrogen or C$_1$-C$_4$ alkyl;
Y is NH or O;
A is a C$_1$-C$_6$ alkylene,
X is an anion.

The thus obtained inverse emulsions possess a stability which is perfectly suited for their industrial use in cosmetic formulations, even many months after their preparation; furthermore the inverse emulsions of the invention enable the preparation of cosmetic formulations with very good compatibility with skin and hair.

It is well known that the combined presence of two different functionalities in the same macromolecule, a cationic one and an anionic one, tends to be the cause of coagulation; coagulation can occur both in the phase preceding the reaction (when monomers having opposed functionality are mixed together), and while the reaction takes place, during the polymer formation.

An insufficient distribution of the charges in the macromolecule itself increases its solubility in the oily phase and leads to its desorption from the water phase where the reaction takes place.

The polymer desorption and its consequent dissolution in the oily phase usually causes the coagulation of the dispersed system and gelation.

It has now surprisingly been observed that by exclusively using anionic acrylic monomers containing a strongly acidic functional group together with cationic monomers, and operating within the ratio of the present invention, it is still possible to prevent coagulation and gelation.

It is a fundamental object of the present invention an inverse emulsion for the preparation of cosmetic formulations wherein the weight ratio between the aqueous phase and the organic phase is from 4:1 to 2:1 and containing from 20 to 70% by weight of an acrylic polymer obtained by inverse emulsion polymerization of:

(i) from 90 to 99.9% by weight, and preferably from 60 to 70% by weight, of an anionic acrylic monomer containing a strongly acidic functional group;
(ii) from 0.1 to 10% by weight of a cationic acrylic monomer of the formula (I):

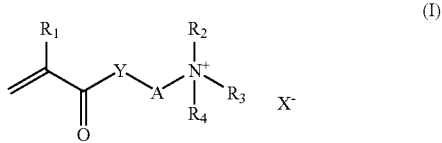

wherein
- $R_1$ is hydrogen or methyl;
- $R_2$, $R_3$, $R_4$ are, one independently of the others, hydrogen or $C_1$-$C_4$ alkyl;
- Y is NH or O;
- A is a $C_1$-$C_6$ alkylene;
- X is an anion.

The anionic acrylic monomer containing a strongly acidic functional group is selected among the monomer of this kind that are normally employed for the preparation of polymeric synthetic thickeners for the cosmetic use; among those, 2-acrylamido-2-methylpropanesulfonic acid is preferred for the realisation of the present invention.

Preferably the cationic acrylic monomer of the formula (I) is selected from acryloyloxyethyl-trimethylammonium chloride and methacryloyloxyethyl-trimethlyammonium chloride. In the general formulas for the cationic acrylic monomers, the X is defined as an anion. This counter ion may be any that will not cause the cationic acrylic monomer to be insoluble or otherwise prevent it from being polymerized. For example, X can be a halide such as a chloride or bromide. While the general formula appears to require the anion to have a −1 charge, it is not so limited. For example, it may be a complex or simple anion having a −2 charge subject to the prior stated requirement that the counter ion not prevent the cationic acrylic monomer from being polymerized.

According to a fundamental aspect of the invention the acrylic polymer obtained by inverse emulsion polymerisation is cross-linked with from 0.01 to % by weight of a compound containing two or more ethylenic groups, preferably with methylene-bis-acrylamide.

It is a further object of the present invention a procedure for the preparation of an inverse emulsion for cosmetic formulations characterised by:
a. preparing a composition consisting of from 40 to 60% by weight of water, and for the remaining percentage by weight of a mixture of acrylic monomers consisting of:
  i. from 90 to 99.9% by weight, and preferably from 60 to 70% by weight, of an anionic acrylic monomer containing a strongly acidic functional group;
  ii. from 0.1 to 10% by weight, and preferably from 2 to 4% by weight, of a cationic acrylic monomer of the formula (I)

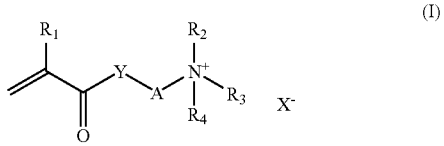

(I)

wherein
- $R_1$ is hydrogen or methyl;
- $R_2$, $R_3$, $R_4$ are, one independently of the others, hydrogen or $C_1$-$C_4$ alkyl;
- Y is NH or O;
- A is a $C_1$-$C_6$ alkylene;
- X is an anion;

b. adding to the composition prepared in a. an aqueous solution of an alkali to regulate the pH between 4 and 7, a cross-linking agent and an initiator of radical polymerisation, maintaining the temperature between 3 and 7° C.;
c. preparing an organic phase containing one or more water-in-oil emulsifiers;
d. introducing the mixture obtained in b. into the organic phase prepared in c. and emulsifying the two phases by vigorous stirring;
e. initiating the polymerisation and completing it maintaining the temperature between 55 and 95° C. under vigorous stirring;
f. cooling the reaction mixture to 35-45° C. and adding an oil-in-water emulsifier.

As it was previously said about the inverse emulsion of the invention, the anionic acrylic monomer containing a strongly acidic functional group is selected among the monomers that are normally employed for the preparation of polymeric synthetic thickeners for the cosmetic use; among those, 2-acrylamido-2 -methylpropanesulfonic acid is particularly preferred for the realisation of the present invention.

Preferably the cationic acrylic monomer of the formula (I) is selected from acryloyloxyethyl-trimethylammonium chloride and methacryloyloxyethyl-trimethylammonium chloride. In the general formulas for the cationic acrylic monomers, the X is defined as an anion. This counter ion may be any that will not cause the cationic acrylic monomer to be insoluble or otherwise prevent it from being polymerized. For example, X can be a halide such as a chloride or bromide. While the general formula appears to require the anion to have a −1 charge, it is not so limited. For example, it may be a complex or simple anion having a −2 charge subject to the prior stated requirement that the counter ion not prevent the cationic acrylic monomer from being polymerized.

In the procedure of the invention, normally, the alkali used is NaOH.

According to another aspect of the invention, the acrylic polymer obtained by inverse emulsion polymerisation is cross-linked with from 0.01 to 1% by weight of a compound containing two or more ethylenic groups, preferably with methylene-bis-acrylamide.

Among the initiators of radical polymerisation utilisable for the realisation of the present invention are ammonium, potassium or sodium persulfate, and water-soluble organic peroxides, by way of example hydrogen peroxide and peracetic acid.

In the inverse emulsions of the invention the organic phase consists of by mineral oils containing saturated hydrocarbons or by vegetable oils or by mixture thereof having boiling point from 150 to 300° C.

Preferably the organic phase is a $C_{20}$ hydrogenated polydecene.

The water-in-oil and the oil-in-water emulsifiers are those normally used for this purpose.

We cite among the utilisable water-in-oil emulsifiers: sorbitan monolaurate, sorbitan monopalmitate, sorbitan monostearate, sorbitan monooleate; among the utilisable oil-in-water emulsifiers we cite the linear or branched ethoxylated alcohols.

To initiate the polymerisation of the acrylic monomers advantageously an aqueous solution of sodium metabisulfite is used.

The inverse emulsions of the invention may further additionally contain the common additives used in radical polymerisation, by way of example sequestering agents such as sodium diethylenetriaminepentaacetate.

As it was previously observed, the inverse emulsions of the present invention are particularly suited for the treatment of hair and skin, in body and face creams, hair gels and lotions, hair colouring and bleaching creams, sunscreen compositions, make-up products, cleansing, moisturizing and perspiring fluids.

In the following examples the preparation of inverse emulsions according to the invention and of some cosmetic formulations containing them is reported.

The examples illustrate the present invention without limiting it, or the kind of application of the inverse emulsions of the invention.

EXAMPLES

Example 1

The following ingredients are loaded into a 1.5 l pirex reactor equipped with a steel anchor stirrer:

693 g aqueous solution (50% by weight) of sodium 2-acrylamido-2-methylpropane sulfonate;

3 g ADAMQUAT MC 80 (acryloyloxyethyl-trimethyl ammonium chloride sold by Atofina).

At about 0° C., the following ingredient are slowly added while stirring:

10 g aqueous solution (2% by weight) of methylene-bisacrylamide;

0.5 g aqueous solution (40% by weight) of sodium diethylenetriaminepentaacetate;

5 g aqueous solution (4% by weight) of ammonium persulfate.

In the meantime, the organic phase is prepared inside a 500 ml beaker adding under stirring:

16.2 g sorbitan monooleate;

204 g $C_{20}$ hydrogenated isodecene.

The aqueous phase is slowly added into the organic phase and subsequently the mixture is efficiently stirred with a high shear dispersing machine (ultra-turrax IKA).

The emulsion obtained is then reloaded in the reactor and the reaction is ready to be started (reaction phase). The first operation is to insufflate nitrogen directly in the bulk of the product for about 10 minutes. This is a key step, because it enables to lower and control the amount of oxygen dissolved in the emulsion and to adjust the induction times. The second phase takes place only after the emulsion temperature is warmed up to 20° C. After that, 10 g of a 1% by weight aqueous solution of sodium metabisulfite is quickly loaded drop-wise through an addition funnel. The third phase is the radical reaction. The reaction proceeds spontaneously raising gradually the temperature to about 50° C. in 50 minutes. The stirring is maintained very fast and cool water re-circulates inside the reactor jacket. After this period of time the emulsion is heated to 60° C. and maintained at this temperature for about one hour to complete the monomers conversion, consuming the residual monomers. Subsequently a cooling down period is required to reach a temperature of 35-40° C. The final step is the addition of 22 g of isotridecylic alcohol 9.5 moles ethoxylated.

The mixture is rapidly stirred till homogeneity is reached; the final emulsion (Emulsion 1) is then unloaded and stored for at least 24 hours before the evaluation of its properties.

Property evaluation of Emulsion 1.

Samples of Emulsion 1 are stored at different temperatures.

The emulsion stability is evaluated at different temperatures by visually checking possible phase separation or settling on the bottom of the vessel using a glass stick.

In the following table (Table 1) the test temperatures and minimal stability times of the emulsion are shown.

TABLE 1

| | Temperature | | |
|---|---|---|---|
| | 5° C. | 20° C. | 45° C. |
| Stability (days) | >360 | >180 | >30 |

The thickening properties are instead evaluated as follows and are shown in Tables 2 and 3.

A 2% by weight aqueous solution of Emulsion 1 is prepared in deionized water with high stirring in a 1 liter beaker.

Subsequently the viscosity is measured at 20° C., at different pH values (see Table 2 Brookfield Viscosity in mPa s, spindle 6, after 24 h).

The pH was adjusted by additions of an aqueous solution (50%) of citric acid.

TABLE 2

Brookfield Viscosity in mPa · s (spindle 6, after 24 h)

| 5 rpm | pH |
|---|---|
| 52000 | 7.4 |
| 50100 | 7.1 |
| 21000 | 6.7 |
| 4500 | 6.5 |
| 950 | 4.3 |

Rpm = rounds per minute

Example 2

A viscous facial freshener for dry skins was prepared with Emulsion 1, with the following ingredients:

TABLE 3

Viscous facial freshener for dry skins

| Ingredient | % |
|---|---|
| Phase A | |
| Water | to 100 |
| Glycerine | 2 |
| *Euphrasia officinalis* inaqua | 5 |
| *Punica granatum* (and) propylene glycol (and) water | 1.5 |
| Diazolidinyl urea | 0.25 |
| Emulsion 1 | 1 |
| Phase B | |
| *Persea Gratissima* oil | 1.9 |
| Bisabolol | 0.1 |
| Fase C | |
| Fragrance | 0.1 |

Phase A is mixed at room temperature and homogenised using a high shear turbo emulsifier. Phase B is prepared, added to Phase A while stirring with the turbo emulsifier. Phase C is added and the mixture is stirred to homogeneity.

Features of the obtained cream:

Viscosity=12600 mPa.s (5 rpm, 20° C.);

pH=6.7;

Stability=no separation after centrifugation at 6000 rpm for 30 minutes at 25° C.

The product shows high spreadability when used. The stoutness of the product and its long lasting effect helps the active substances absorption

The invention claimed is:

1. An inverse emulsion comprising an aqueous phase and an organic phase, wherein
   the weight ratio of the aqueous phase to the organic phase is from 4:1 to 2:1 and
   the inverse emulsion includes from 20 to 70% by weight of an acrylic polymer consisting essentially of the inverse emulsion polymerization of:
   (i) from 90 to 99.9% by weight of an anionic acrylic monomer containing a strongly acidic functional group;
   (ii) from 0.1 to 10% by weight of a cationic acrylic monomer of the formula (I):

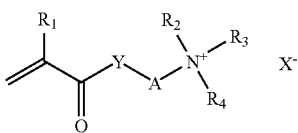

wherein:
   $R_1$ is hydrogen or methyl;
   $R_2$, $R_3$, and $R_4$ are, one independently of the others, hydrogen or $C_1$-$C_4$ alkyl;
   Y is NH or O;
   A is a $C_1$-$C_6$ alkylene;
   X is an anion; and
   wherein the acrylic polymer obtained by inverse emulsion polymerization is cross-linked with from 0.01 to 1% by weight of a compound containing two or more ethylenic groups.

2. The inverse emulsion of claim 1, wherein the anionic acrylic monomer containing a strongly acidic functional group is 2-acrylamido-2-methylpropanesulfonic acid.

3. The inverse emulsion of claim 1, wherein the X in the general formula for the cationic acrylic monomer is a halide.

4. The inverse emulsion of claim 3, wherein the X in the general formula for the cationic acrylic monomer is a chloride.

5. The inverse emulsion of claim 4, wherein the cationic acrylic monomer of the formula (I) is selected from acryloyloxyethyl-trimethylammonium chloride and methacryloyloxyethyl-trimethylammonium chloride.

6. The inverse emulsion of claim 2, wherein the acrylic polymer obtained by inverse emulsion polymerization is cross-linked with methylene-bis-acrylamide.

* * * * *